US012752270B2

(12) United States Patent
Kim et al.

(10) Patent No.: US 12,752,270 B2
(45) Date of Patent: Oct. 6, 2026

(54) MICROSTRUCTURE AND MOLECULAR DETECTION METHOD

(71) Applicants: NATIONAL INSTITUTE OF ADVANCED INDUSTRIAL SCIENCE AND TECHNOLOGY, Tokyo (JP); KOREA UNIVERSITY RESEARCH AND BUSINESS FOUNDATION, Seoul (KR)

(72) Inventors: Hyonchol Kim, Tsukuba (JP); Dai Kato, Tsukuba (JP); Chikashi Nakamura, Tsukuba (JP); Man Bock Gu, Seoul (KR); Cheul Min Joe, Seoul (KR)

(73) Assignees: NATIONAL INSTITUTE OF ADVANCED INDUSTRIAL SCIENCE AND TECHNOLOGY, Tokyo (JP); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 689 days.

(21) Appl. No.: 18/017,632

(22) PCT Filed: Jul. 29, 2021

(86) PCT No.: PCT/JP2021/029040

§ 371 (c)(1),
(2) Date: Jan. 23, 2023

(87) PCT Pub. No.: WO2022/025297

PCT Pub. Date: Feb. 3, 2022

(65) Prior Publication Data

US 2023/0294088 A1 Sep. 21, 2023

(30) Foreign Application Priority Data

Jul. 30, 2020 (JP) ................................ 2020-129235

(51) Int. Cl.
*B01L 3/00* (2006.01)
*G01N 21/64* (2006.01)
(Continued)

(52) U.S. Cl.
CPC .. *B01L 3/502707* (2013.01); *G01N 33/54326* (2013.01); *G01N 33/553* (2013.01); *B01L 2300/08* (2013.01); *G01N 2021/6432* (2013.01)

(58) Field of Classification Search
None
See application file for complete search history.

(56) References Cited

U.S. PATENT DOCUMENTS

2005/0277125 A1* 12/2005 Benn ...................... B01L 3/563 435/287.2
2008/0176757 A1* 7/2008 Hassibi ............... C12Q 1/6851 506/7

(Continued)

FOREIGN PATENT DOCUMENTS

JP 2008528973 A 7/2008
JP 2009535060 A 10/2009

(Continued)

OTHER PUBLICATIONS

Translation of JP-2015031596-A, Ueno Yuko, Feb. 16, 2015 (Year: 2015).*

(Continued)

*Primary Examiner* — Henry H Nguyen
(74) *Attorney, Agent, or Firm* — James S. Keddie; Bozicevic, Field & Francis LLP

(57) ABSTRACT

To provide a microstructure equipped with a mechanism for selectively detecting marker molecules expressed or secreted by individual cells forming a cell population, a method for fabricating such a microstructure, and specific
(Continued)

solutions for detecting and identifying molecules to be detected using such a microstructure, the present invention provides a method for fabricating a hemispherical shell-shaped microstructure made of a thin film of a desired thickness and diameter, in which a material surface capable of fixing a probe for detecting a biomolecule is arranged on the inner surface, and a method for detecting a target biomolecule using such a thin film.

18 Claims, 5 Drawing Sheets

(51) Int. Cl.

*G01N 33/543* (2006.01)
*G01N 33/553* (2006.01)

(56) References Cited

U.S. PATENT DOCUMENTS

| | | | | |
|---|---|---|---|---|
| 2009/0213369 | A1* | 8/2009 | Lee | B82Y 5/00 424/617 |
| 2010/0022011 | A1* | 1/2010 | Swager | G01N 21/643 436/128 |
| 2011/0092380 | A1* | 4/2011 | Stahler | B01J 19/0046 506/13 |
| 2013/0277278 | A1 | 10/2013 | Day et al. | |
| 2015/0299758 | A1 | 10/2015 | Yasuda et al. | |
| 2019/0317084 | A1* | 10/2019 | Shepard | G01N 27/4146 |

FOREIGN PATENT DOCUMENTS

| | | | | |
|---|---|---|---|---|
| JP | 2011-101941 | A | | 5/2011 |
| JP | 2014233208 | A | | 12/2014 |
| JP | 2015031596 | A | * | 2/2015 |
| WO | WO 2013/069732 | A1 | | 5/2013 |

OTHER PUBLICATIONS

Oberhaus et al., "Immobilization Techniques for Aptamers on Gold Electrodes for the Electrochemical Detection of Proteins: A Review", Biosensors, Apr. 27, 2020, 10(5), 45 (Year: 2020).*

Ren et al., "Made-to-order nanocarbons through deterministic plasma nanotechnology", Nanoscale, Nov. 16, 2010, 3, 731-740 (Year: 2010).*

Arita, "Analysis of the Secretion from Single Anterior Pituitary Cells by Cell Immunoblot Assay", Endocrine Jurnal, 1993, 40(1): 1-15.

International Search Report issued for International Application No. PCT/JP2021/029040, mailed Oct. 19, 2021.

Ueno et al., "Molecular design for enhanced sensitivity of a FRET aptasensor built on the graphene oxide surface", Chemical Communications, 2013, 49: 10346-10348.

Office Action issued on Aug. 27, 2024 for corresponding Japanese Application No. 2020-129235.

Sun et al., "A Conjugated Aptamer-Gold Nanoparticle Fluorescent Probe for Highly Sensitive Detection of rHuEPO-α", Sensors, Nov. 2011, 11: 10490-10501.

Wang et al., "Aptamer biosensor for protein detection using gold nanoparticles", Analytical Biochemistry, 2008, 373: 213-219.

Written Decision on Registration (Notice of Allowance), issued for Korean Application No. 10-2023-7006678, Dec. 29, 2025.

* cited by examiner

MICROSTRUCTURE AND MOLECULAR DETECTION METHOD

CROSS-REFERENCE TO RELATED APPLICATIONS

This application is a § 371 national phase of International Application No. PCT/JP2021/029040, filed on Jul. 29, 2021, which claims the benefit of Japanese Application No. 2020-129235, filed on Jul. 30, 2020, which applications are incorporated by reference herein.

TECHNICAL FIELD

The present invention relates to a microstructure having a structure such as a hemispherical shell or a semi-elliptical shell, which is composed of a laminated material of two or more thin films having different materials on an inner surface and an outer surface, and a substance detection method using the microstructure.

BACKGROUND OF THE INVENTION

Microstructures such as microparticles are widely used as materials for developing materials having new physical properties and as labels for visualizing target proteins or DNA in the life sciences. Though spherical microparticles, which are generally easily produced, are widely used, microparticles having a complicated shape such as ellipse and polygon have wide applications due to their anisotropy in optical properties, and the development of the production method of such microparticles is actively promoted.

Japanese Patent Application Publication No. 2011-101941 ("Hollow Microparticles and Method for Producing the Same") (Patent Document 1) discloses a method for producing a hemispherical shell-shaped microparticle shaped like a bowl, and Japanese Patent Application Publication No. 2011-101941 ("Magnetic Nanoparticles") (Patent Document 2) discloses a method for producing hemispherical shell-shaped microparticles with magnetic materials and applying the hemispherical shell-shaped microparticles to a cell-purification technique.

Japanese Patent Application Publication No. 2011-101941 (Patent Document 1) discloses a method of manufacturing hemispherical shell-shaped microparticles by forming a metal thin film on polystyrene particles arranged on a flat substrate by vacuum evaporation or sputtering and removing the polystyrene particles by chemical treatment, heating, or the like. However, specific applications of the produced microparticles in the field of life sciences, in particular, applications for detecting biomolecules such as proteins and DNA, which are important in medical diagnostics, are not shown.

In WO2013/069732 (Patent Document 2), as one of the applications of the method of Japanese Patent Application Publication No. 2011-101941 (Patent Document 1), there is disclosed a method of preparing hemispherical shell-shaped particles of the same size as cells (about 10 μm in diameter) using a magnetic material such as nickel or iron, trapping a cell in the inner depression of the microparticle in a size-selective manner for purification and recovery. In order to produce hemispherical-shell particles, a method for producing superparamagnetic particles has been developed by placing an insulating layer between magnetic thin films. However, no method has been shown for identifying cell types and properties beyond cell recovery, especially by detecting biomolecules expressed on the surface of recovered cells.

Among biomolecules, secretions secreted by cells have recently attracted attention as "message substances," and the type and amount of secretions is an important indicator that reflects the "personality" of the cell. Cells interact with surrounding cells via secretions to create a suitable environment for themselves or to adapt to the surrounding environment. For example, in tumor tissues, cancer cells are thought to create a favorable microenvironment for their growth by influencing the surrounding normal cells through secretions. Therefore, the precise measurement of the substances secreted by individual cells in a cell population on a cell-by-cell basis is important for the elucidation of disease mechanisms and the discovery of novel therapeutic targets.

There are several techniques for measuring secretion in single cells, such as Jun Arita, "Analysis of the Secretion from Single Anterior Pituitary Cells by Cell Immunoblot Assay", Endocrine Journal, Vol. 40, 1, 1-15 (1993) (Non-Patent Document 1), in which cells are cultured on a sheet of fixed antibodies that capture secretions, and the secretions released from the cells and captured by the antibodies are later stained and visualized. In Patent Publication 2014-233208 ("Comprehensive Cell Secretion Fluid Analysis Apparatus and Method") (Patent Document 3), the amount of secretion of each cell is measured by capturing each cell in a tiny chamber of several tens of microns and detecting that the secretions released from each cell have accumulated and concentrated in the chamber. However, both methods disclose only methods for measuring the secretions of individual cells that are completely isolated, where adjacent cells are separated from each other, and no means for measuring the secretions of individual cells in a networked and interacting cell population are disclosed.

On the other hand, in order to detect a particular biomolecule, it is useful to use a probe switch that produces no reaction when the biomolecule is not present, but only produces a signal (e.g., fluorescence) when the biomolecule is present. For this purpose, aptamer molecules are often used. Ueno et al., "Molecular design for enhanced sensitivity of a FRET aptasensor built on the graphene oxide surface", Chem. Commun., 49, 10346-10348, (2013) (Non-Patent Document 2) shows a method of biomolecule detection using aptamer probes modified with fluorescent dyes and graphene membranes. When a fluorescent aptamer is fixed on a flat graphene surface, the distance between the fluorophores and the graphene surface becomes close because the aptamer adsorbs to the graphene surface, resulting in fluorescence quenching due to the fluorescence resonance energy transfer (FRET) between the fluorophores and graphene. In other words, sensing techniques have been shown to detect the presence of target biomolecules as the generation of fluorescence. However, because graphene is ultra-flat at the atomic level, it is difficult to form a continuous large-area thin film on a curved surface. In addition, Non-Patented Document 2 describes a method for detecting biomolecules in solution by mounting the sensing technology on a microfluidic device but does not describe a method for detecting biomolecules expressed by individual cells or secretions released.

PRIOR ART DOCUMENTS

Patent Document 1: Japanese Patent Application Publication No. 2011-101941 Patent Document 2: WO2013/069732

Patent Document 3: Japanese Patent Application Publication No. 2014-233208

Non-Patent Document 1: Jun Arita, "Analysis of the Secretion from Single Anterior Pituitary Cells by Cell Immunoblot Assay", Endocrine Journal, Vol. 40, 1, 1-15 (1993)

Non-Patent Document 2: Ueno et al., "Molecular design for enhanced sensitivity of a FRET aptasensor built on the graphene oxide surface", Chem. Commun., 49, 10346-10348, (2013)

SUMMARY OF THE INVENTION

Problem to be Solved by the Invention

Therefore, it is desirable to provide a microstructure provided with a mechanism for selectively detecting marker molecules expressed or secreted by individual cells forming a cell population, a method for producing the microstructure, and a specific solution for detecting and identifying molecules to be detected using the microstructure.

Means for Solving the Problem

In view of the above situation, the present invention provides a method for producing a hemispherical shell-shaped microstructure made of a thin film of a desired thickness and diameter, in which a material surface capable of fixing a probe for detecting a biomolecule is arranged on its inner surface, and a method for detecting a target biomolecule by using it. The present invention also provides a method for producing and controlling a microstructure whose outer surface is composed of a magnetic material and whose orientation can be controlled by applying an external magnetic field, a method for producing a microstructure whose inner surface is a thin-film structure having an $SP^2$ hybrid orbital or a metal thin-film structure capable of molecular fixation and capable of producing a fluorescent FRET, and a method for fluorescence detection of a target molecule by a selective reaction of a target biomolecule with a protein, peptide, or nucleic acid molecule that emits fluorescence due to a change in molecular structure fixed on the inner surface after trapping a biomolecule or a cell in the above microstructure.

More specifically, the present disclosure includes the following Items [1] to [21]:

[1] A hemispherical shell-shaped hollow-multilayered microstructure for use in the detection of a target molecule, comprising:

a first thin film layer in the form of a substantially micro-hemispherical shell composed of a first material comprising a magnetic material, and a second thin film layer disposed on the inner surface of the micro-hemispherical shell and composed of a second material, wherein said second material comprises a material capable of removably fixing a fluorochrome-labeled probe and causing fluorescence resonance energy transfer between the fluorochrome and the material, wherein a hollow space defined by the second thin film layer has a size that is capable of capturing at least one cell of the target or a portion thereof in said hollow space, and wherein the probe is a molecule capable of specific binding to the target molecule, and said binding to the target molecule can alter the structure of the probe, thereby causing a change in emission/quenching of the fluorochrome.

[2] The hemispherical shell-shaped hollow multilayer microstructure according to Item [1], wherein the first material comprises a magnetic material selected from the group consisting of nickel, iron, cobalt, gadolinium, ruthenium, iron oxide, chromium oxide, ferrite and neodymium.

[3] The hemispherical shell-shaped hollow-multilayered microstructure according to Item [1] or [2], wherein the second material comprises an element having an $SP^2$ hybrid orbital, an element in which an $SP^2$ bonded region and an $SP^3$ bonded region are mixed, or a metal.

[4] The hemispherical shell-shaped multilayer microstructure according to Item [3], wherein the second material comprises nanocarbon, nanographene or gold.

[5] The hemispherical shell-shaped multilayer microstructure according to Item [4], wherein the second thin film layer has an amino group on its surface.

[6] The hemispherical shell-shaped multilayer microstructure of any one of Items [1] to [5], wherein the probe is a protein, peptide, or nucleic acid molecule.

[7] The hemispherical shell-shaped multilayer microstructure according to Item [6], wherein the probe is a nucleic acid molecule modified with a fluorochrome at one end and a pyrene molecule or thiol group at the other end.

[8] The hemispherical shell-shaped multilayer microstructure of any one of Items [1] to [7], wherein the target molecule comprises a protein, peptide, nucleic acid, cell surface molecule or cell secretory vesicle.

[9] The hemispherical shell-shaped hollow multilayer microstructure according to any one of Items [1] to [8], wherein the film thickness of each thin film layer is in the range of 0.1 nm to 1 mm.

[10] An array of hemispherical shell-shaped hollow multilayer microstructures comprising a hemispherical shell-shaped hollow multilayer microstructure according to any one of Items [1] to [9].

[11] The hemispherical shell-shelled hollow multilayer microstructure or the array thereof according to any one of Items [1] to [10], comprising said probe removably fixed to a surface of said second thin film layer.

[12] The hemispherical shell-shaped multilayer microstructure or array thereof according to Item [11], wherein the probe is removably fixed to the surface of the second thin film layer via a spacer molecule and/or wherein the fluorochrome is bound to the probe via the spacer molecule.

[13] A method of producing a hemispherical shell-shaped hollow multilayer microstructure or array thereof for use in the detection of a target molecule according to any one of Items [1] to [12], comprising the steps of:

a) providing mold microparticles of a desired size arranged in a single layer on a substrate, said mold microparticles consisting of a material removable by a predetermined removal process, b) coating the mold microparticles arranged on the substrate with the second material in the single layer, c) further coating the mold microparticles coated with the second material with the first material, and d) removing the mold particles by the predetermined removal process to obtain the hemispherical shell-like hollow multilayer microstructure.

[14] The method according to Item [13], wherein said method further comprises at least one step of coating with a further material between step b) and step c).

[15] The method according to Item [13] or [14], wherein said method further comprises:

transferring the hemispherical shell-shaped hollow multilayer microstructure from the substrate surface to an adhesive surface after said step d), and/or removably fixing said probe to said second thin film layer.

[16] The method according to Item [14], wherein the further material comprises a material comprising an element or an alloy of elements different from the first or second material.

[17] The method according to Item [15], wherein the adhesive is a soluble adhesive.

[18] The method according to Item [17], wherein said soluble adhesive is polydimethylsiloxane and comprises solubilizing said adhesive in a solvent.

[19] A method for detecting a target molecule using at least one hemispherical shell-shaped multilayer microstructure or array thereof according to Item [11] or [12] or at least one hemispherical shell-shaped multilayer microstructure or array thereof produced by the producing method as claimed in Item [15], [17] or [18], comprising:

a) placing the hemispherical shell-shaped hollow multilayer microstructure or array thereof comprising the probe removably fixed to the second thin film layer in a solution containing or suspected of containing the target molecule and b) measuring fluorescence emission of the fluorochrome of the probe, wherein binding between the target molecule and the probe is estimated by detecting the fluorescence emission, and the presence of the target molecule in the solution is determined.

[20] The method according to Item [19], comprising:

controlling the orientation of the hemispherical shell-shaped hollow multilayer microstructure dispersed in the solution by applying an external magnetic field in step a).

[21] The method according to Item [19] or [20], wherein the target molecule is a secretion of a cell, and said method comprises the step of trapping the cell or a portion thereof in a hollow space of the hemispherical shell-shaped multilayer microstructure between steps a) and b).

Effect of the Invention

Prior to the present invention, there was no technology that could measure the secretion of a single cell in a network of cells individually. According to the present invention, it is possible to identify the type and amount of substances secreted by individual cells forming a population. For example, in a biopsy performed in the case of a suspected disease, a portion of tissue is taken to examine the characteristics of individual cells, and the present invention can be a simple test method for identifying diseased cells, etc. using secretions as an indicator. In other words, it is expected to lead to the development of techniques to distinguish between cancer cells and other cells by secretion. In addition, the present invention is not limited to disease testing, but can also be applied to the detection of specific substances and microorganisms in the environment.

BRIEF DESCRIPTION OF THE DRAWINGS

FIG. 3-1 shows an example of a method to detect a target molecule using a DNA aptarner attached with a fluorescent dye. FIG. 3-2 shows an example of a method to detect a target molecule using a DNA aptamer attached with a fluorescent dye and a pyrene group.

FIG. 5-1 shows an example of a method to detect a target molecule using a fluorescent aptamer fixed on the inner surface of a microstructure with an inner surface of Au. FIG. 5-2 shows an example of a method to detect a target molecule by adsorbing a fluorescent aptamer onto a microstructure with nanographene fixed on its inner surface.

FIG. 6-1 shows an example of a method for detecting a target molecule using microstructures aligned in an array on a substrate. FIG. 6-2 shows an example of a method to detect a target molecule using a microstructure attached to the tip of a microscopic cantilever. FIG. 6-3 shows an example of a method to detect a target molecule by attaching magnetic microstructures dispersed in solution to a cell.

EMBODIMENTS FOR IMPLEMENTING THE INVENTION

1. Hemispherical Shell-Shaped Hollow Multi-Layered Microstructures for the Detection of Target Molecules In one aspect, the present invention provides a hemispherical shell-shaped hollow multilayered microstructure (hereinafter simply referred to as a "microstructure") for use in the detection of target molecules. The microstructure of the present invention comprises a first thin film layer in the form of a substantially micro-hemispherical shell comprising a first material comprising a magnetic material and a second thin film layer disposed on the inner surface of said micro-hemispherical shell, comprising a second material comprising a material capable of removably fixing a probe labeled with a fluorescent dye and producing a fluorescence resonance energy transfer (FRET) between the material and the fluorescent dye. Typically, the microstructure of the present invention has a hollow space thereof sized to capture at least one cell of interest or a portion thereof, and said probe disposed in a second thin film layer is a molecule that can specifically bind to a target molecule and whose binding to the target molecule can change its structure, thereby causing a change in the emission/quenching of the fluorescent dye.

Figure 1:
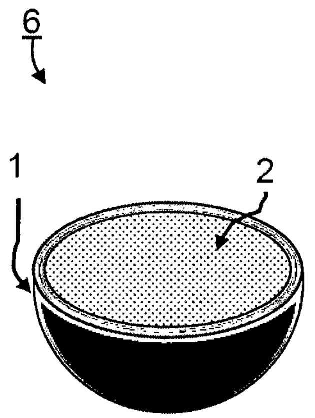
FIG. 1 shows a schematic diagram of a microstructure with a two-layered structure as one aspect of the invention.

FIG. 1 illustrates an example of a microstructure 6 of the present invention. In this example, a hemispherical shell-like microstructure 6 with a two-layer structure comprising a magnetic metal thin film as the first thin film layer 1 and a nanocarbon thin film as the second thin film layer 2 is shown, but the number of layers is not limited to two layers, and a thin film layer of different elements or elemental alloys may be sandwiched between multiple layers as an intermediate layer. When the target molecule is detected by fluorescence ON/OFF switch, the inner surface (second thin film layer) may be a thin film structure comprising an element having $SP^2$ hybrid orbital, an element in which $SP^2$ bonded region and an $SP^3$ bonded region are mixed, or a metal (i.e., the second material) that is capable of molecular fixation and fluorescence FRET, but in other cases, it is not limited to this category. The first material comprised in the first thin film layer may be typically a magnetic material (e.g., ferromagnetic material, superparamagnetic material) that includes, but is not limited to, a metal such as nickel, iron, cobalt, gadolinium or ruthenium, or an alloy such as a metallic oxide (e.g., iron oxide, chromium oxide), ferrite or neodymium. Exemplary examples of the second material include nanocarbons, nanographene, and gold. When gold is used as the second material, an amino group may be added to the gold forming the second thin film layer in order to make the surface of the second thin film layer positively charged, as shown in the embodiment described hereinbelow, thereby, optionally, for example, facilitating the binding of negatively charged DNA aptamers to the surface of the second thin film layer.

When referring to "magnetic material" with respect to the present invention, the term "magnetic material" is used in the ordinary sense in which it is used in the art. For the purpose of the present invention, it is desirable that the "magnetic material" used in the present invention is magnetic to the extent that the orientation of the microstructure can be controlled by the magnetic field when an external magnetic field is applied.

The film thickness of the thin film is freely selectable to the extent that the structure of the microstructure 6 can be retained, and the film thickness per layer is typically from about 0.1 nm to 1 mm, more preferably from about 1 nm to 10 and most preferably from about 1 nm to 1 μm, but it is not limited to these ranges and may be determined as appropriate for the purpose. In addition, the shape of the microstructure varies according to the shape of the mold at the time of microstructure preparation, and can be hemispherical, cylindrical, conical, elliptical, angular, etc., but is not limited to this range. It will be understood from the description herein that, for example, the mold particulates themselves for creating the hemispherical shell-shaped microstructure 6 need not necessarily be hemispheric in shape, but may be spherical. As used herein, the term "substantially hemispherical," "substantially hemispherical shell-shaped," or "substantially spherical" shall, unless otherwise specified, include all of the shapes exemplified herein or the shell shapes thereof, as well as those having a distortion of shape that would be acceptable in an actual manufacturing situation. The size (diameter) of the microstructure can also be varied according to the shape of the mold at the time of fabrication, and is in the range of about 1 nm to about 1 cm, preferably about 1 nm to about 500 μm, more preferably about 5 nm to about 100 μm, and most preferably about 10 nm to about 50 μm. The size (diameter) of the hollow portion (concave side cavity portion) of the hemispherical shell-shaped structure of the microstructure of the invention can also be freely made according to the shape of the mold, and is in the range of about 1 nm to about 1 cm, preferably from about 1 nm to about 500 μm, more preferably from about 5 nm to about 100 μm, and most preferably from about 10 nm to about 50 μm. Typically, the size of the cavity can be a size (diameter) that is capable of accepting at least a single cell or a portion thereof.

With respect to the present invention, "cells of interest" are typically cells obtained from mammals, including humans (e.g., humans, cows, pigs, goats, sheep, monkeys, dogs, cats, mice, rats, etc.), but may also include, without limitation, cells from birds, reptiles, amphibians, insects, microorganisms, plants, etc.

2. Method for Manufacturing Hemispherical Shell-Shaped Hollow Multilayered Microstructures for Use in the Detection of Target Molecules The present invention also provides, in another aspect, a method for manufacturing the microstructure of the present invention. This manufacturing method includes the following steps:

(a) preparing mold particles of the desired size disposed in a single layer on the substrate, (b) covering the mold particles disposed on the said substrate in the single layer with a second material, wherein
(c) further coating the mold particles coated with the second material with a first material; and
(d) removing said mold particles by a predetermined removal process, and obtaining a hemispherical shell-shaped hollow multilayered microstructure.

Exemplarily, the above mold particles comprise a material that can be removed by a predetermined removal process. Optionally, between step b) and step c) above may further comprise at least one step of coating with another material, and after step d) above may comprise a step of transferring the said hemispherical shell-shaped hollow multilayered microstructure from the surface of the said substrate to the surface of the said adhesive, using an adhesive, and/or a step of removably fixing the probe to the second thin film layer.

Exemplary requirements for the first material, the second material, and the probe are as described in Section 1 above with respect to the microstructures of the present invention.

Figure 2:
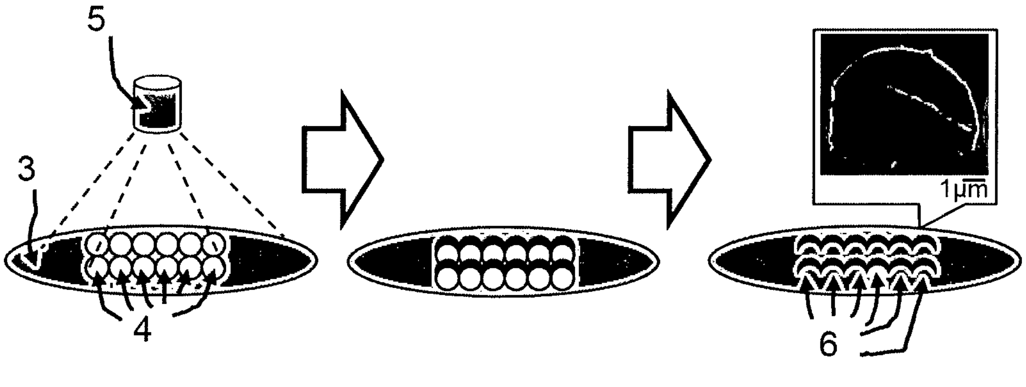
FIG. 2 shows a schematic diagram of a method for fabricating a microstructure as one mode of this invention.

FIG. 2 illustrates an exemplary example of a method of producing a microstructure 6 of the present invention. Initially, a single layer of microparticles 4, which serve as a mold, is placed on the flat substrate 3. The material for the flat substrate 3 can be glass, silicon, plastic, etc., but as long as the surface flatness is smaller than the size of the mold particles 4, it is not limited to this range, and any substrate can be used according to the purpose. The mold particles 4 may be polystyrene, cellulose or glass particles, but this range is not limited as long as they are of the same size and shape as the desired microstructure. In addition, the size of the mold particles 4 may range from about 1 nm to about 1 cm, typically from about 1 nm to about 500 μm, more typically from about 5 nm to about 100 μm, and most typically from about 10 nm to about 50 μm, depending on the size of the microstructure desired to be produced. A flat substrate loaded with mold particulates 4 is placed in the sample chamber of the thin film forming apparatus 5, which is capable of forming a thin film material inside the microstructure 6.

The thin-film forming apparatus 5 may be a sputtering apparatus, a resistance heating vacuum evaporator, a chemical vapor deposition apparatus, or the like, but it is not limited thereto as long as the apparatus is capable of forming a thin film with a film thickness in any range of about 0.1 nm to 1 mm, which is no larger than the size of the mold particles.

In the case of nanocarbon thin films, an unbalanced magnetron sputtering system is used, which is capable of forming carbon films with mixed $SP^2$ and $SP^3$ bonded regions. The ratio between the $SP^2$ and $SP^3$ bonded regions can be freely adjusted by sputtering conditions.

For a sample installed in a sample room, a thin film of the inner material is formed on top of the mold particulates 4 on the flat substrate 3 by preparing a thin film of any thickness for the inner material according to the procedure for using the thin film forming apparatus 5. Next, this sample is placed in the sample chamber of the thin film formation apparatus 5, which is capable of forming a magnetic metal thin film on the outer side of the microstructure, and the thin film is formed in the same way as the inner film formation. This results in the formation of a two-layered thin film, as shown in FIG. 1, on top of the mold particles 4. If the number of thin-film layers is more than three, this procedure is repeated to increase the number of layers. After forming a thin film of a multilayered structure on top of the mold particles 4 according to the above procedure, the mold particles 4 are removed to obtain a microstructure 6 as shown in FIG. 1.

The methods for removing the mold particulates 4 may include high-temperature heating, organic solvent treatment, reactive oxygen treatment, and the like. In one example, the mold polystyrene particles can be removed by heating the mold polystyrene particles at 500° C. for one hour, but this range is not limited thereto as long as the mold particles 4 are removed by the method and the thin layer is not removed. When preparing magnetic microstructures, the mold particles may be removed in an atmosphere with an oxygen concentration of 15% or less in order to maintain the magnetic moment.

3. Method for Detecting Target Molecules Using the Microstructure of the Present Invention The present invention further provides, in another aspect, a method for detecting a target molecule using at least one microstructure of the present invention or an array thereof, or at least one microstructure of the present invention or an array thereof manufactured by a method of manufacturing the microstructure of the present invention. This method typically includes the following steps:

(a) placing a hemispherical shell-shaped hollow multilayered microstructure or array thereof comprising a probe removably fixed to a second thin film layer in a solution containing or suspected of containing a target molecule, and (b) measuring the emission of fluorescence of a fluorescent dye of said probe.

Typically, the detection of the above-mentioned fluorescence emission will infer the binding of the target molecule to the probe and confirm the presence of the target molecule in solution.

Exemplary requirements for a second thin film layer and probe are as described in the description of the microstructure of the present invention in Section 1 above. In addition, the term "array" is used in the sense normally used in the relevant field, and when the term "array of microstructures" is used with respect to the present invention, it means a population of microstructures in which two or more microstructures are arranged in one or two dimensions (see, for example, FIGS. 2, 4, 6-1, 6-3, etc.).

Figure 3:
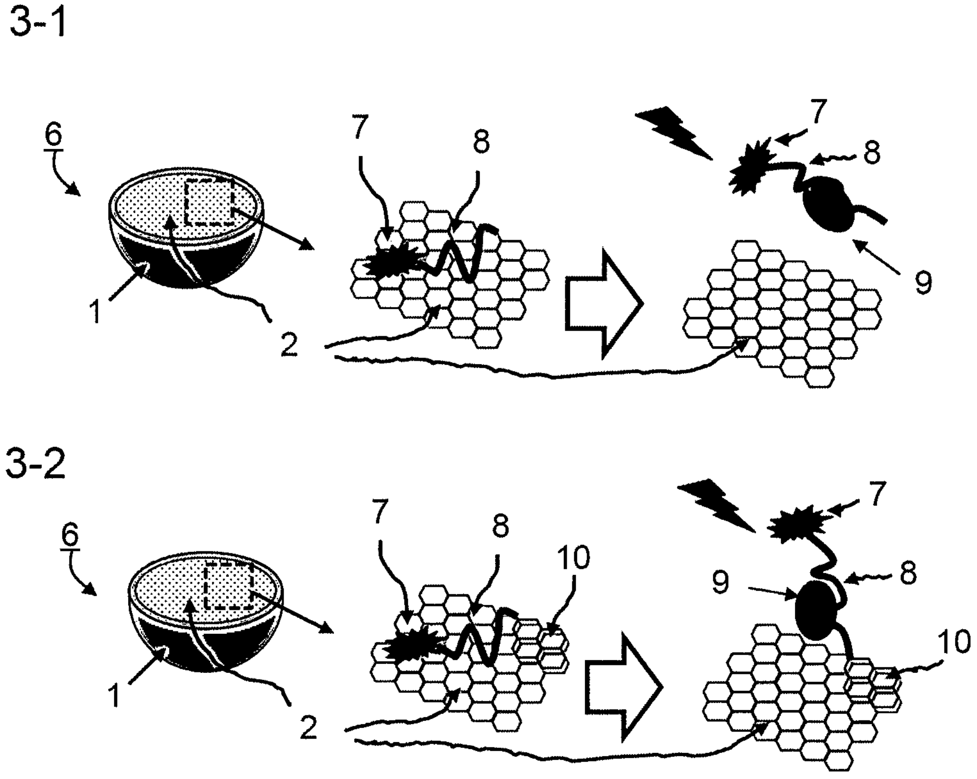
FIG. 3 shows a schematic diagram of a method for detecting a target molecule using a fluorescent aptamer fixed on the inner surface of a microstructure whose inner surface is a nanocarbon film, as one aspect of the present invention.

FIG. 3 illustrates an example of a method for detecting a target molecule by a selective reaction between a protein, peptide, or nucleic acid molecule as a probe and the target molecule. Here, as a non-limiting example, a DNA aptamer modified with a fluorescent dye is used as a probe and a nanocarbon film is used as a second thin film layer. It should be noted that, as used herein, the term "aptamer" is used in the sense normally used in the art and means a generic term for a peptide or nucleic acid molecule that is capable of binding to a particular molecule.

FIG. 3-1 shows a non-limiting example using a DNA aptamer 8 with a fluorescent dye molecule 7 modified at either end and a microstructure 6 in which the inner surface thin film (second thin film layer) 2 is a nanocarbon thin film. The length of the DNA aptamer 8 can be varied according to the purpose. Typically, this range is from about 80 to 100 nucleotides, but it is not limited to this range and may include 10, 20, 30, 40, 50, 60, 70, 80 nucleotides as non-limiting examples of lower limits, 90, 100, 110, 110, 120, 130, 140, 150 nucleotides, or more as non-limiting examples of upper limits, and the optimal range may be selected from a combination of these lower and upper limits as appropriate for the purpose.

In the non-limiting example of the present invention shown in FIG. 3-1, when aptamer 8 is mixed with microstructure 6, the DNA main strand of aptamer 8 has an affinity with the surface of nanocarbon thin film 2, so that aptamer 8 adsorbs on the surface of nanocarbon thin film 2, resulting in fluorescence resonance energy transfer (FRET) as fluorescent dye 7 approaches the surface of nanocarbon thin film 2, resulting in the absence of fluorescence from fluorescent dye 7. When the target molecule 9 binds to the aptamer 8, the binding of the target molecule 9 to the aptamer DNA main strand dissociates the aptamer 8 from the nanocarbon film 2, and the fluorescent dye molecule 7 also dissociates from the surface of the nanocarbon film 2, resulting in FRET dissociation and fluorescence. In other words, the presence of the target molecule 9 can be detected by the fluorescence produced from within the electrode microstructure 6 where the target molecule 9 is present.

FIG. 3-2 shows a non-limiting example using a DNA aptamer 8 modified with a pyrene molecule 10 having a cyclic structure at one end and a fluorescent dye molecule 7 at the other end and a microstructure 6 whose inner film 2 is a nanocarbon film. When said aptamer 8 is mixed with said microstructure 6, the $SP^2$ bonded region of the nanocarbon thin film 2 and the pyrene molecule 10 are bound together by n-n interaction, and as a result, the aptamer 8 can be fixed on the inner side of the microstructure 6. Moreover, since the DNA main chain of aptamer 8 has an affinity with the surface of nanocarbon film 2, aptamer 8 adsorbs on the surface of nanocarbon film 2 (the molecule lies down), and as a result, the fluorescent dye 7 is close to the surface of nanocarbon film 2, resulting in the formation of a fluorescent FRET and the absence of fluorescence from the fluorescent dye 7. When the target molecule 9 binds to the aptamer 8, the binding of the target molecule 9 to the aptamer DNA main chain changes the structure of the aptamer 8 (the molecule stands up), and the FRET is dissolved as the fluorescent dye 7 moves away from the surface of the nanocarbon film 2, resulting in the generation of fluorescence. That is, the presence of the target molecule 9 can be detected by fluorescence from the inner surface of the electrode microstructure 6.

Any molecule that can bind to aptamers can be detected, including but not limited to proteins, peptides, nucleic acids, cell surface molecules, and cell secretory vesicles. In addition, although DNA aptamers are used as an example in FIG. 3, different types of aptamers such as RNA aptamers, proteins, and peptides can be used to for the detection by the same principle. Furthermore, it is easy to understand that a target molecule can be detected not only by an aptamer but also by any molecule that can selectively bind to the target molecule and whose fluorescence emission or quenching changes due to changes in its molecular structure, using a similar principle. In FIG. 3-2, the aptamer was fixed on the surface of a nanocarbon thin film via a pyrene molecule, but the number of carbon-six-membered ring structures is not limited to four as in the case of the pyrene molecule and may be two, three, or four or more as long as the aptamer can be fixed by a π-π bond. The minimum number of fixable carbon-six-membered ring structures is determined by the size of the aptamer molecule, but for example, if the base number of DNA aptamer is 80, 4 (pyrene molecule) is sufficient for the fixation.

Regarding the difference between FIG. 3-1 and FIG. 3-2, in FIG. 3-1, the number of aptamer 8 molecules adsorbed on the microstructure 6 surface decreases as the target molecule 9 binds, because aptamer 8 dissociates from the microstructure 6 surface due to the binding of the target molecule 9. On the other hand, the fluorescent dye 7 is sufficiently far from the microstructure 6 surface that the changes in fluorescence emission and quenching become clearer than in the case of FIG. 3-2, and the introduction of the pyrene molecule 10 into aptamer 8 is not necessary, so the preparation of the molecule is easy and relatively inexpensive. On the other hand, in FIG. 3-2, the distance of the fluorescent dye molecule 7 away from the surface of the microstructure 6 is more limited than in FIG. 3-1, but as a solution, a spacer may be introduced between the fluorescent dye 7 and the DNA aptamer 8 or between the DNA aptamer 8 and the pyrene molecule 10. In this way, the dissociation distance between the fluorescent dye molecule 7 and the surface of the microstructure 6 can be increased when the target molecule 9 binds and the structure of the aptamer 8 is changed. As spacer molecules, polymeric polypeptides such as polyethylene glycol, stranded molecules such as DNA, RNA, etc. can be used. The spacer length can be in the range of about 0.1 nm to about 30 μm, typically in the range of about 0.1 nm to about 1 μm, but is not limited to these ranges as long as it can be achieved with polymers, polypeptides, nucleic acid molecules, etc.

Figure 4:
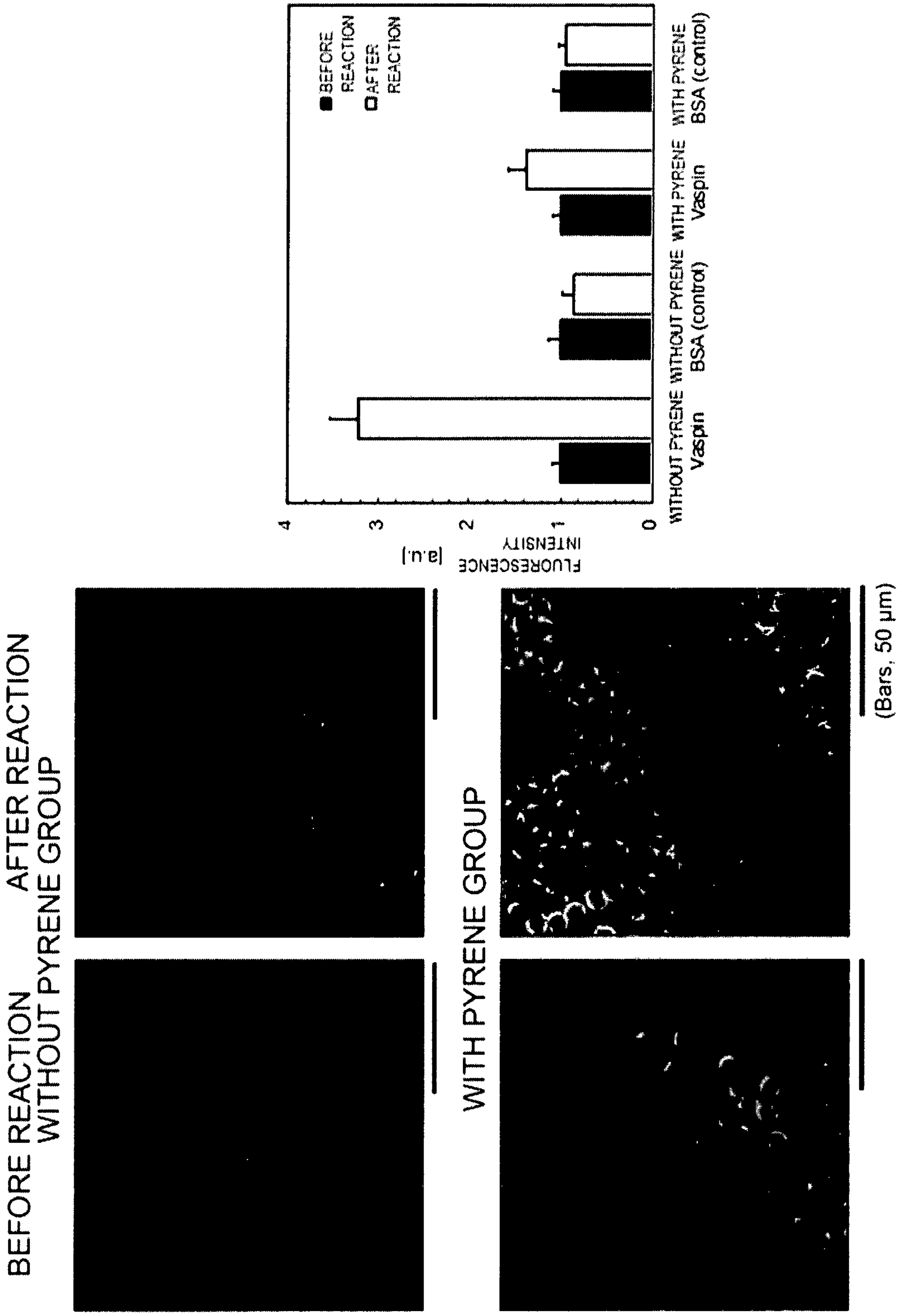
FIG. 4 shows a representative example of a fluorescence microscope image of a target molecule, vaspin, detected by using a DNA aptamer attached to a fluorescent dye or a DNA aptamer attached to a fluorescent dye and a pyrene group, which is fixed on the inner surface of a microstructure as one of the modes of the present invention, and a graph comparing the change in fluorescence intensity based on the image.

FIG. 4 shows a non-limiting example of biomolecule detection using the fluorescent DNA aptamer described in FIG. 3, where vaspin, one of the biomolecules, was detected. As shown in FIGS. 3-1 and 3-2, the fluorescent DNA aptamer, which is a complex of fluorescent dye 7 and aptamer 8 and, in the case of FIG. 3-2, pyrene molecule 10, was fixed on the inner surface of a microstructure 6 with a diameter of 15 μm, a nanocarbon thin film on the inner surface, and nickel on the outer surface, and the fluorescence intensity before and after the vaspin reaction was compared when vaspin solution was added to it. The addition of the target molecule 9, vaspin, increased the fluorescence intensity in both FIG. 3-1 and FIG. 3-2 compared to the pre-reaction level. When bovine serum albumin (BSA) was added as a control, no change in fluorescence intensity was observed before and after the reaction. These results demonstrate that the presence or absence of a target molecule can be detected selectively as a change in fluorescence intensity using fluorescent DNA aptamers.

Figure 5:
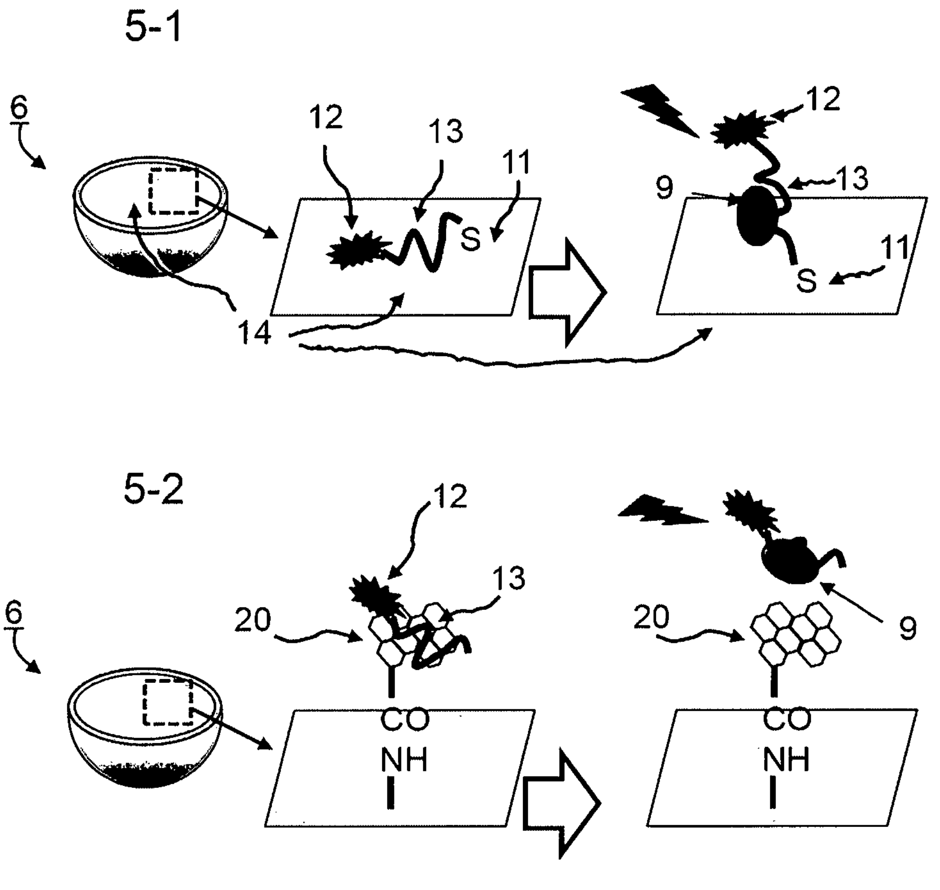
FIG. 5 shows a schematic diagram of another example of a method for detecting a target molecule using a fluorescent aptamer fixed on the inner surface of a microstructure as an embodiment of the present invention.

FIG. 5 shows a non-limiting example of a method for detecting target biomolecules on the inner surface of a thin film other than the nanocarbon film shown in FIG. 3.

FIG. 5-1 shows an example of biomolecule detection on gold (Au) surface 14, where DNA aptamer 13 with a thiol group (S) at one end and a fluorescent dye 12 at the other end is mixed with a microstructure 6 with an inner surface of Au, where the DNA aptamer 13 is fixed to the Au surface 14 on the inner surface of the microstructure 6 via the thiol group (S). Since the DNA base has an affinity for the Au surface, the DNA aptamer 13 adsorbs on the Au surface 14, resulting in FRET, which quenches the fluorescence. When the target molecule 9 binds to it, the structure of DNA aptamer 13 changes, and fluorescence is generated, as in FIG. 3-2, and the presence of the target molecule 9 can be detected. Furthermore, the Au surface 14 may be positively charged by surface treatment, such as attaching an amino group to the Au surface 14, so that the negatively charged DNA aptamer 13 is adsorbed on the Au surface 14 by electrostatic interaction and FRET is generated. In the case of attaching an amino group to the Au surface 14, an alkyl chain having an amino group at one end and a thiol group at the other end may be prepared and mixed in the same way as for fixing DNA aptamer 13 to a microstructure 6 having an inner surface of Au. By premixing DNA aptamer 13 with an alkyl chain having an amino group and a thiol group attached to it in any ratio beforehand and mixing it with the microstructure 6 having an inner surface of Au and fixing it, an alkyl chain having DNA aptamer 13 and an amino group attached to it may be fixed on the Au surface 14 in any ratio. The alkyl chain length can range from about 0.1 nm to about 20 nm, typically from about 0.1 nm to about 5 nm, taking into account the efficiency with which FRET occurs.

FIG. 5-2 shows a non-limiting example of a method for detecting target molecules 9 by fixing nanographene 20, a nano-sized graphene film, to an amino group on the inner surface of a microstructure 6. In this case, the fluorescent aptamers (12, 13) are not tightly fixed to the nanographene 20, e.g., by covalent bonding, but the aptamers 13 are adsorbed to the surface of the nanographene 20. Binding of target molecule 9 changes the structure of aptamer 13, as in FIG. 3-1, and its dissociation from the surface of nanographene 20 results in fluorescence. In this example, the aptamer 13 is dissociated, but the target molecule 9 can be detected with high sensitivity as shown in FIG. 4. The method of introducing an amino group on the inner surface of the microstructure 6 can be realized by having the material on the inner surface of the microstructure 6 be a material having a hydroxyl group, such as silicon dioxide, and reacting thereon with a silane coupling agent, such as 3-Aminopropyltriethoxysilane, or by fixing the alkyl chain having the aforementioned amino group on the Au surface. In the case of FIG. 5-2, when an alkyl chain having an amino group is used to introduce an amino group, the alkyl chain length can be in the range of about 0.1 nm to about 30 μm, typically in the range of about 0.1 nm to about 1 μm, because there is no need to consider the efficiency of FRET formation. Furthermore, the material for the chain portion connecting the amino group and the thiol group may be a polymer, polypeptide, nucleic acid molecule, etc., in addition to the alkyl chain.

Figure 6:
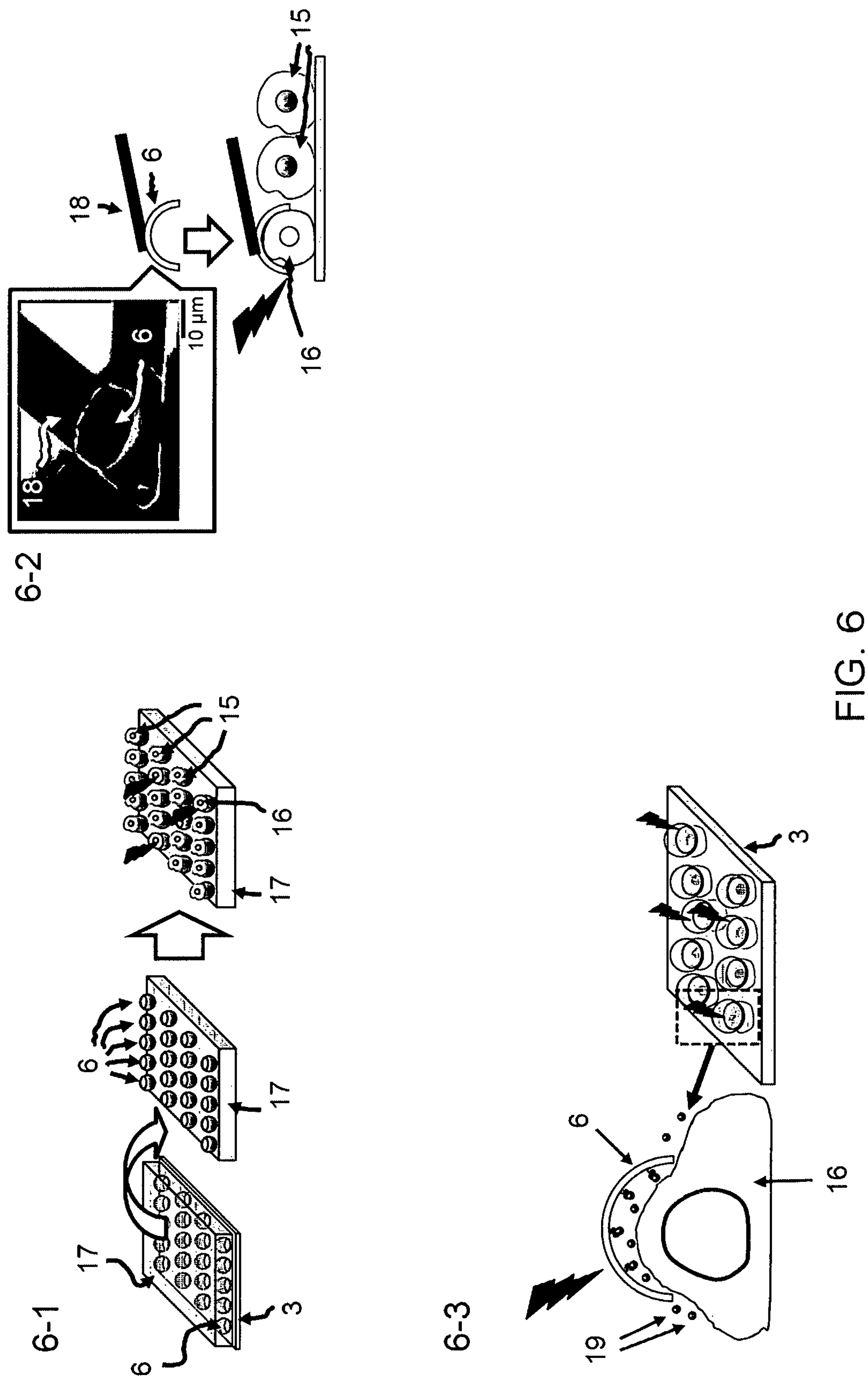
FIG. 6 shows a schematic diagram of a method for detecting a target molecule using a microstructure with a fluorescent aptamer fixed on its inner surface as one aspect of the present invention.

FIG. 6 shows, as a non-limiting example of detection of specific biomolecules, a method for detecting secretions secreted by a cell by microstructures with fixed fluorescent aptamers. In this example, for a mixture of general cells 15 that do not secrete a target molecule and target cells 16 that secrete a target molecule, fluorescence is shown only from a hemispherical shell-like microstructure 6 that traps the target cell 16. Three embodiments are shown in FIG. 6.

FIG. 6-1 illustrates a procedure for trapping and detecting cells in each microstructure 6 in an array of microstructures 6 on a substrate 3. Arranging the microstructure 6 in an array form can be achieved by transferring the microstructure 6 onto the adhesive 17 by applying and peeling off the adhesive 17 from the top of the microstructure 6 on the substrate 3 fabricated in the procedure of FIG. 2.

FIG. 6-2 illustrate a configuration in which a microstructure 6 is attached to the tip of a microscopic cantilever and the microstructure 6 is covered over a cell attached on the substrate 3 for detection. As a small cantilever beam, e.g., cantilever 18 of an atomic force microscope may be used.

FIG. 6-3 show a configuration in which the microstructure 6 having magnetism is dispersed in solution and then, by application of a magnetic field, the microstructure 6 is attached to a cell attached to the substrate and secretion 19 is detected. In this case, a micro-structure 6 of the same size as the prominence of the cell (about 5 μm in diameter) to be adhered on the substrate 3 is prepared, the microstructure 6 is dispersed in the solution, and then the microstructure 6 is attached to the cell by accumulating the micro-structure 6 in the direction of the cell by applying a magnet from the backside of the substrate 3 to which the cell is attached. Because the microstructure 6 does not cover the entire cell surface, the uncoated cell surface can receive secretions 19 from other cells, allowing the response of the cell to stimuli from the surrounding environment to be measured.

It goes without saying that the inner surface of the microstructure 6 used in FIGS. 6-1 to 6-3 is pre-fixed with probe molecules such as fluorescent aptamers for detecting the target molecule 19.

In the case of dispersing the microstructure 6 fabricated in FIG. 2 into a solution, the microstructure 6 is detached from the substrate 3 by dropping a desired solution onto the substrate 3 and applying ultrasound from the backside of the substrate 3, so the method of dispersing the microstructure 6 into the solution is effective, but on the other hand, the problem of some of the microstructure 6 being destroyed by ultrasound may occur. A means of solving this problem is to apply and peel off a solubilizable adhesive 17 on the microstructure 6 on the substrate 3 fabricated in FIG. 2. After transferring the microstructure 6 onto the surface of the adhesive 17 as shown in FIG. 6-1, the solubilization treatment is performed by placing the adhesive 17 in a tube, and the solution-dispersed microstructure 6 is obtained by dissolving the adhesive 17. For example, when polydimethylsiloxane (PDMS) is adhered to the substrate 3 of FIG. 2 and removed, microstructure 6 is transferred to the surface of the PDMS. When this PDMS is placed in a tube and isopropanol is added to the tube, the surface of the PDMS is solubilized and the microstructure 6 is dispersed in the isopropanol. By recovering this and replacing it with any solution, a microstructure 6 dispersed in solution without damage can be obtained. Regarding the "solubility" of the adhesive, solubility in organic solvents was explained above, but it is not limited thereto.

The technical scope of the invention is not limited to these specific examples described above, and various variations are possible within the technical scope of the invention and its equivalents described in the attached claims, and these variations are also included in the technical scope of the invention.

INDUSTRIAL APPLICABILITY

The microstructures of the present invention, the biomolecules (including those modified with fluorescent dyes, etc.) attached to the microstructures, and combinations thereof, as well as manufacturing methods, control methods, and methods of use thereof, are applicable to various fields, and are particularly useful in the fields of environmental test chips, such as the detection of substances and microorganisms in the environment, in the field of cellular diagnostics, such as the detection of specific cells in a plurality of cells, and in the field of blood liquid biopsy, such as the detection of specific cells in the blood.

EXPLANATION OF THE SYMBOLS

1: First thin film layer, 2: Second thin film layer, 3: Flat substrate, 4: Mold microparticle, 5: Thin-film formation apparatus, 6: Microstructure, 7: Fluorescent dye, 8: DNA aptamer, 9: Target molecule, 10: Pyrene molecule, 11: Thiol group, 12: Fluorescent dye, 13: DNA aptamer, 14: Au thin film, 15: Standard cell that does not secrete target molecule, 16: Target cell that secretes target molecule, 17: Adhesive, 18: Atomic force microscope cantilever, 19: Secretion, 20: Nanographene.

The invention claimed is:

1. A hemispherical shell-shaped hollow-multilayered microstructure for use in detection of a target molecule, comprising:

a first thin film layer in the form of a substantially micro-hemispherical shell composed of a first material comprising a magnetic material, and a second thin film layer disposed on the inner surface of the micro-hemispherical shell and composed of a second material, wherein said second material is capable of removably fixing a fluorochrome-labeled probe and causing fluorescence resonance energy transfer between the fluorochrome and the second material, wherein the second material is nanocarbon in which an SP2 bonded region and an SP3 bonded region are mixed, wherein a hollow space defined by the second thin film layer has a size that is capable of capturing at least one cell of the target molecule or a portion thereof in said hollow space, and wherein the fluorochrome-labeled probe is a molecule capable of specific binding to the target molecule, and said binding to the target molecule can alter the structure of the fluorochrome-labeled probe, thereby causing a change from quenching to emission of the fluorochrome, wherein the hemispherical shell-shaped hollow multilayer microstructure comprises said fluorochrome-labeled probe removably fixed to a surface of said second thin film layer, wherein the fluorochrome-labeled probe is a nucleic acid molecule modified with the fluorochrome at one end and a pyrene molecule at the other end, and wherein the fluorochrome is bound to the fluorochrome-labeled probe via a spacer molecule.

2. The hemispherical shell-shaped hollow multilayer microstructure according to claim 1, wherein the first material comprises a magnetic material selected from the group consisting of nickel, iron, cobalt, gadolinium, ruthenium, iron oxide, chromium oxide, ferrite and neodymium.

3. The hemispherical shell-shaped multilayer microstructure according to claim 1, wherein the second thin film layer has an amino group on its surface.

4. The hemispherical shell-shaped multilayer microstructure of claim 1, wherein the target molecule comprises a protein, peptide, nucleic acid, cell surface molecule or cell secretory vesicle.

5. The hemispherical shell-shaped hollow multilayer microstructure according to claim 1, wherein the film thickness of each thin film layer is in the range of 0.1 nm to 1 mm.

6. An array of hemispherical shell-shaped hollow multilayer microstructures comprising a hemispherical shell-shaped hollow multilayer microstructure according to claim 1.

7. The hemispherical shell-shaped hollow multilayer microstructure according to claim 1, wherein the spacer molecule is introduced between the fluorochrome and the nucleic acid molecule or between the pyrene molecule and the nucleic acid molecule.

8. The hemispherical shell-shaped hollow multilayer microstructure according to claim 7, when the target molecule binds to the fluorochrome-labeled probe, a binding of the target molecule to the fluorochrome-labeled probe changes a structure of the fluorochrome-labeled probe, and a fluorescence resonance energy transfer is dissolved as the fluorochrome moves away from the surface of the second thin film layer, resulting in a generation of fluorescence.

9. The hemispherical shell-shaped hollow multilayer microstructure according to claim 7, wherein the spacer molecule is polyethylene glycol, DNA, or RNA.

10. A method of producing a hemispherical shell-shaped hollow multilayer microstructure for use in detection of a target molecule according to claim 1, comprising steps of:

a) providing mold microparticles of a desired size arranged in a single layer on a substrate, said mold microparticles consisting of a material removable by a predetermined removal process, b) coating the mold microparticles arranged on the substrate with the second material in the single layer, c) further coating the mold microparticles coated with the second material with the first material, and d) removing the mold particles by the predetermined removal process to obtain the hemispherical shell-like hollow multilayer microstructure.

11. The method according to claim 10, wherein said method further comprises at least one step of coating with a further material between step b) and step c).

12. The method according to claim 10, wherein said method further comprises:

transferring the hemispherical shell-shaped hollow multilayer microstructure from the substrate surface to an adhesive surface after said step d), and/or removably fixing said fluorochrome-labeled probe to said second thin film layer.

13. The method according to claim 11, wherein the further material comprises a material comprising an element or an alloy of elements different from the first or second material.

14. The method according to claim 12, wherein the adhesive surface is a soluble adhesive.

15. The method according to claim 14, wherein said soluble adhesive is polydimethylsiloxane and comprises solubilizing said soluble adhesive in a solvent.

16. A method for detecting a target molecule using at least one hemispherical shell-shaped multilayer microstructure according to claim 1, comprising:

a) placing the hemispherical shell-shaped hollow multilayer microstructure comprising the fluorochrome-labeled probe removably fixed to the second thin film layer in a solution containing or suspected of containing the target molecule and b) measuring fluorescence emission of the fluorochrome of the fluorochrome-labeled probe, wherein binding between the target molecule and the fluorochrome-labeled probe is estimated by detecting the fluorescence emission, and presence of the target molecule in the solution is determined.

17. The method according to claim 16, comprising:

controlling orientation of the hemispherical shell-shaped hollow multilayer microstructure dispersed in the solution by applying an external magnetic field in step a).

18. The method according to claim 16, wherein the target molecule is a secretion of a cell, and said method comprises the step of trapping the cell or a portion thereof in a hollow space of the hemispherical shell-shaped multilayer microstructure between steps a) and b).

* * * * *